(12) United States Patent
Lederer

(10) Patent No.: US 8,064,980 B2
(45) Date of Patent: Nov. 22, 2011

(54) INITIATING A SCAN IN A MEDICAL IMAGING SYSTEM

(75) Inventor: Wayne Lederer, Atlantic Beach, NY (US)

(73) Assignee: Wayne Lederer, Atlantic Beach, NY (US)

( * ) Notice: Subject to any disclaimer, the term of this patent is extended or adjusted under 35 U.S.C. 154(b) by 801 days.

(21) Appl. No.: 11/850,976

(22) Filed: Sep. 6, 2007

(65) Prior Publication Data

US 2008/0064948 A1    Mar. 13, 2008

Related U.S. Application Data

(60) Provisional application No. 60/843,469, filed on Sep. 7, 2006.

(51) Int. Cl.
*A61B 5/05* (2006.01)

(52) U.S. Cl. ........ 600/407; 600/410; 600/413; 600/418; 600/425; 200/56 R; 378/204; 324/318

(58) Field of Classification Search .................. 600/410, 600/413, 418, 407, 425; 200/56 R; 378/204; 324/318
See application file for complete search history.

(56) References Cited

U.S. PATENT DOCUMENTS

| | | | |
|---|---|---|---|
| 4,458,689 A | 7/1984 | Sorenson et al. | |
| 5,276,747 A | 1/1994 | Pan | |
| 5,363,844 A | 11/1994 | Riederer et al. | |
| 5,519,675 A | 5/1996 | Toofan | |
| 5,825,951 A | 10/1998 | Kitamura | |
| 6,118,236 A * | 9/2000 | Shaw et al. | 318/136 |
| 6,400,155 B2 * | 6/2002 | Kormos et al. | 324/318 |
| 6,972,751 B2 | 12/2005 | Sadahiro | |
| 7,055,190 B2 | 6/2006 | Barth et al. | |
| 7,199,582 B2 | 4/2007 | Keegan et al. | |
| 2003/0098844 A1 * | 5/2003 | Melnyk | 345/156 |
| 2005/0139787 A1 | 6/2005 | Chiba et al. | |
| 2006/0114986 A1 | 6/2006 | Knapp et al. | |

OTHER PUBLICATIONS

GE Healthcare Brochure, *Signa 1.5T MR*, 18 pages (2006).

* cited by examiner

*Primary Examiner* — Long V Le
*Assistant Examiner* — Jason Ip
(74) *Attorney, Agent, or Firm* — Fish & Richardson P.C.

(57) ABSTRACT

A method of initiating a scan in a medical imaging device includes detecting a patient-ready signal from a magnetically and radiographically inert communication device and automatically initiating the scan upon detecting the patient-ready signal.

12 Claims, 1 Drawing Sheet

INITIATING A SCAN IN A MEDICAL IMAGING SYSTEM

CROSS-REFERENCE TO RELATED APPLICATIONS

This application claims the benefit of priority from a U.S. Provisional Patent Application No. 60/843,469 filed on Sep. 7, 2006. The disclosure of that application is incorporated herein by reference.

BACKGROUND

This disclosure relates to a communication device for use in a medical imaging system.

During magnetic resonance imaging (MRI) and computed tomography (CT) scanning procedures, it is often necessary to provide the patient in an MRI or CT machine with instructions or information regarding a scan procedure. For example, in certain circumstances, it is desirable to instruct a patient to hold their breath and remain still so that acceptable scans can be obtained. To facilitate this, some machines utilize software driven voice command systems which audibly instruct patients to hold their breath for precisely timed periods in preparation for one or more scans. Following delivery of the instruction, the automated system initializes the scan. However, it is often the case that a patient is not ready once the scan begins. Subsequently, motion artifacts may appear in the resulting scan image, thus requiring the scan to be repeated. Repeating scans is time-consuming and results in increased hospital costs as well as increased patient stress.

SUMMARY

Various aspects of the invention are set forth in the claims.

For example, in one aspect, an apparatus for use in a medical imaging system includes a magnetically and radiographically inert communication device, a sensor coupled to the communication device and a processor coupled to the sensor. The processor is operable to initiate a scan by the medical imaging system upon activation of the communication device.

In another aspect, a method of initiating a scan in a medical imaging device includes detecting a patient-ready signal from a magnetically and radiographically inert communication device and automatically initiating the scan upon detecting the patient-ready signal.

Some implementations include one or more of the following features. For example, the communication device can be hand-held. In some cases, the sensor is operable to detect a patient-ready signal that is generated by the communication device.

In some implementations, the detection of the patient-ready signal includes detecting a change in air pressure or an absolute pressure level. The communication device can include a pneumatic actuation device. In addition, the apparatus can include a pneumatic coupler coupled to the communication device and to the sensor. In some cases, the sensor includes a pressure sensor that can detect a change in pressure or an absolute pressure level.

In some implementations, detection of the patient-ready signal includes detecting an optical signal or a change in an optical signal. For example, the optical signal can include a polarization state of the optical signal or a change in light intensity. The communication device can include an optical switch. Alternatively or in addition, the communication device may include a polarizer. In another example, the apparatus includes an optical waveguide, in which the optical waveguide is coupled to the communication device and the sensor. In some cases, the apparatus includes an optical transmitter and/or an optical detector which can detect changes in light intensity. In some cases, the optical detector can detect a change in a polarization state of light.

In some implementations, automatically initiating the scan includes modifying the patient-ready signal to be compatible with the medical imaging device and transmitting the modified patient-ready signal to the medical imaging device. Other features and advantages will be apparent from the detailed description and drawings, and from the claims.

DETAILED DESCRIPTION

MRI imaging and CT scans are useful diagnostic tools that enable non-invasive analysis of internal structures and flows within a patient's body. Generally, MRI entails the application of radio frequency waves to a patient's body in a region of changing magnetic field such that the molecules within the patient's body resonate at detectable frequencies. The detected frequencies are processed to enable imaging of internal and external structures. CT scanning entails the generation of a three-dimensional image of a patient's internal structures from a large series of two-dimensional X-ray images taken around a single axis of rotation.

One common application of MRI and CT scanning is in breath-hold imaging studies, which can be very important in medicine and medical research. Breath-hold imaging is a technique in which the patient holds his breath during one or more imaging scans. By holding his breath, the patient minimizes respiratory movement that can cause image artifacts in abdomen and thoracic imaging procedures. Breath-hold imaging requires the full cooperation of the patient as the scan time can extend from 15 to 20 seconds in duration. In some cases, it is necessary for a patient to practice breath holding outside the scanner so that they can improve their response during the examination. However, in many instances, image degradation due to respiratory motion or movement from the patient remains a significant problem because of the length of time necessary to acquire image data. These problems are exacerbated in automated imaging systems that begin scanning when a patient is not ready or is still moving.

Figure 1:
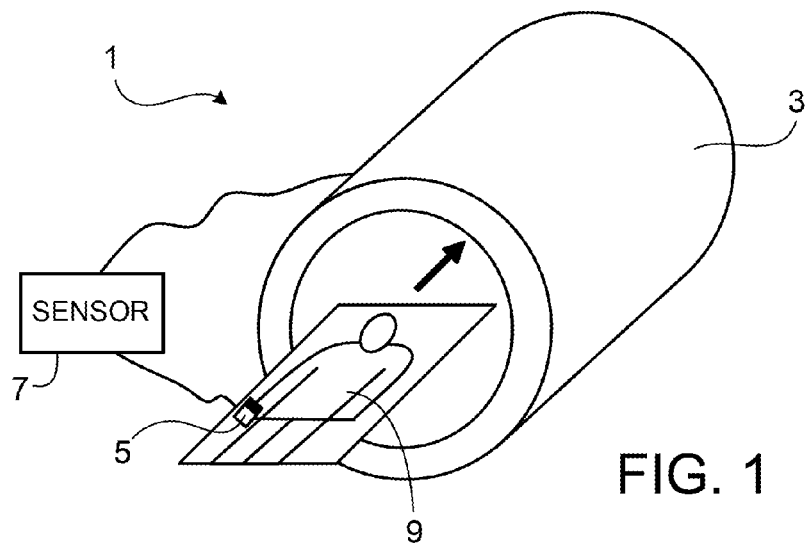
FIG. 1 illustrates an example of an imaging system.

FIG. 1 shows an example of an imaging system 1 which includes a communication device 5 to allow a patient 9 to signal readiness for a scanning procedure to begin. The system 1 includes a MRI machine 3 into which the patient 9 enters. In some implementations, a CT scan machine is used in place of the MRI machine 3. After entering the machine 3, an automated program within the system 1 audibly or visually may request the patient 9 to indicate that they are prepared for the scanning to begin. When the patient 9 is ready, the patient activates the device 5 in response to the request such that a patient-ready signal is sent to a sensor 7 coupled with the device 5. Upon receiving and detecting the patient-ready signal, the sensor 7 outputs a data signal to the MRI machine 3 to activate the scanning procedure. The output of the sensor 7 can be any data signal that is compatible with a scanning device. For example, in some cases, the sensor 7 modifies the patient-ready signal such the data signal output by the sensor 7 corresponds to an ASCII text data, a TTL voltage signal, or an optical signal. Other signal formats and types may be used as well.

Preferably, the communication device 5 is a hand-held device with a simple activation mechanism 6 such as, for example, a push-button or switch. In addition, the device 5 should be formed from non-ferrous, magnetically inert and radiographically inert materials that do not interact with the high magnetic fields of the MRI machine 3 or the X-rays of a CT scanner. Similarly, the patient-ready signals generated by the communication device 5 also should not interact with the high magnetic fields generated by the MRI machine 3 or X-rays generated by a CT scanner.

Figure 2:
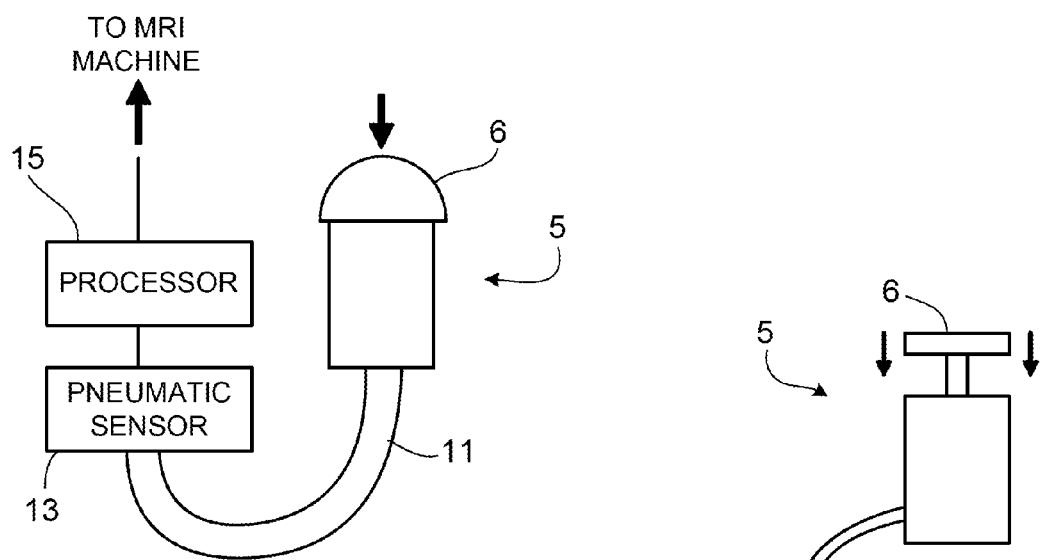
FIG. 2 illustrates an example of a hand-held communication device.

FIG. 2 shows an example of a hand-held communication device 5 in a first embodiment that utilizes pneumatic action. The device 5 includes as the activation mechanism 6 a pliable mushroom cap that, when depressed, causes a change in air pressure within the device 5. The device 5 is coupled to a conduit 11, such as a pneumatic tube, that transfers the change in air pressure to a pneumatic sensor 13. The pneumatic sensor 13 can be any type of pressure sensor or pressure-differential sensor that is able to detect absolute pressure or changes in air pressure caused by activation of the device 5. The sensor 13 is coupled to a processor 15 which is responsible for initiating the image scanning and activation of the machine 3. Upon detecting the change in air pressure or upon detecting a desired air pressure level, the sensor 13 generates and sends a signal, such as an electric potential or current, to the processor 15. After receiving the signal, the processor 15 then activates the image scanning procedure. In some implementations, the pneumatic sensor 13 is combined with the processor 15 as part of a computer. Alternatively, the sensor 13 is a separate component which can be coupled to or removed from a computer that includes the processor 15. In some cases, the sensor 13 is directly coupled to the machine 3 such that the signal provided by the sensor 13 initiates the scan.

Other mechanisms for generating a change in air pressure also may be used. For example, the pliable mushroom cap can be replaced with a plunger mechanism that, when depressed, increases the pressure within the device 5. This increase in pressure then can be transmitted along the pneumatic tube 11 to the sensor 13.

Figure 3:
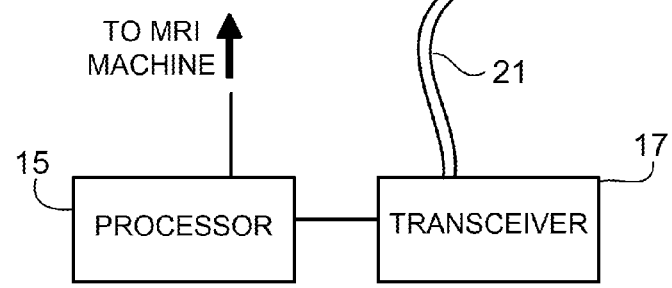
FIG. 3 illustrates an example of a hand-held communication device.

In another embodiment, the hand-held communication device 5 generates a patient-ready signal by interrupting an optical communication link as shown, for example, in FIG. 3. In that example, a transceiver 17 generates an optical signal that is transmitted along an optical path to the communication device 5 by means of a waveguide 21, such as an optical fiber. The optical signal then travels back from the device 5, also by means of the waveguide 21, and is detected by the transceiver 17. The optical signal can be generated using components such as a light emitting diode or laser diode whereas detection can be accomplished using components such as a photodiode or solar cell. Other components for optical generation and detection may be used as well. The optical generation and detection components can be integrated on a single device or used as separate discrete devices. Furthermore, the optical waveguide 21 can include either a single waveguide or separate waveguides for transmission and detection of the optical signal.

When the communication device 5 is in an inactive state, there is no interruption in the optical path and the transceiver 17 outputs a signal to the processor 15 indicating that the patient is not ready for the scan to begin. The signal sent to the processor 15 can include, for example, a fixed voltage or electric current. Upon activation of the device 5, however, the optical path is interrupted and the transceiver 17 no longer detects light from the waveguide 21. Accordingly, the output signal from the transceiver 17 changes state to indicate that the patient is ready for the scan to begin. The output signal from the transceiver 17 can include, for example, a voltage or current level that is substantially different from the signal output by the transceiver 17 when the device has not been activated. The processor 15 coupled to the transceiver 17 detects the change in output signal and initiates the scan. Alternatively, the transceiver 17 can be coupled directly to the machine 3 such that the transceiver output signal initiates the scan.

In another implementation, the optical path can be restored upon activation of the communication device 5. For example, when the device 5 is in an inactive state, it may block transmission of light to the receiver portion of the transceiver 17. When the patient activates the device 5, however, the optical path is restored and an optical signal is delivered to the transceiver 17.

Various different mechanisms can be used to interrupt the optical path. In some implementations, the communication device 5 includes a mechanical optical switch that, depending on activation or deactivation of the device 5, deflects or absorbs the light in the optical path. For example, the device 5 can include a lens in the optical path that translates or rotates to a different position when the patient depresses the push button 6 on the device 5. Depending on the direction of translation/rotation, the optical signal will either travel through the waveguide 21 and return to the transceiver 17 or will be refracted away from the transceiver 17. Similarly, the lens can be replaced with a mirror that also can be translated or rotated. For example, when the device 5 is inactive, the mirror, in a first state, is operable to reflect incoming light back to the transceiver 17. Upon activation of the device 5, the mirror can be rotated or repositioned to a second state such the light is no longer reflected back to the transceiver 17.

In another implementation, activation of the communication device 5 alters the state of the optical signal as opposed to interrupting the optical path. For example, the communication device 5 can include a polarizer that, upon activation of the device 5, changes the polarization of the light traveling along the optical path. Upon detection of the change in polarization, the transceiver 17 outputs a signal indicating that the patient is prepared for the scan to begin.

A number of embodiments of the invention have been described. Nevertheless, it will be understood that various modifications may be made without departing from the spirit and scope of the invention. Accordingly, other implementations are within the scope of the claims.

What is claimed is:

1. A method of initiating a scan in a medical imaging system, the method comprising:
   detecting a patient-ready signal from a manually activated communication device, wherein the communication device is magnetically and radiographically inert; and
   initiating the scan upon detecting the patient-ready signal, wherein a patient manually activates the communication device to generate the patient-ready signal;
   wherein the patient is in the medical imaging system when manually activating the communication device.

2. The method according to claim 1 wherein detecting the patient-ready signal comprises detecting a change in air pressure.

3. The method according to claim 1 wherein detecting the patient-ready signal comprises detecting an absolute pressure level.

4. The method according to claim 1 wherein detecting the patient-ready signal comprises detecting an optical signal.

5. The method according to claim 1 wherein detecting the patient-ready signal comprises detecting a change in an optical signal.

6. The method according to claim 5 wherein detecting a change in an optical signal comprises detecting a change in a polarization state of the optical signal.

7. The method according to claim 5 wherein detecting a change in an optical signal comprises detecting a change in light intensity.

8. The method according to claim 1 wherein automatically initiating the scan comprises modifying the patient-ready signal to be compatible with the medical imaging system and transmitting the modified patient-ready signal to the medical imaging system.

9. The method according to claim 1 wherein the patient manually activates the communication device in response to an automated instruction to initiate the scan.

10. The method according to claim 9 wherein the automated instruction includes a visual instruction.

11. The method according to claim 9 wherein the automated instruction includes an audio instruction.

12. The method according to claim 1 wherein initiating the scan comprises initiating a scan in a magnetic resonance imaging system or in a computed tomography imaging system.

\* \* \* \* \*

UNITED STATES PATENT AND TRADEMARK OFFICE
CERTIFICATE OF CORRECTION

| | | |
|---|---|---|
| PATENT NO. | : 8,064,980 B2 | Page 1 of 1 |
| APPLICATION NO. | : 11/850976 | |
| DATED | : November 22, 2011 | |
| INVENTOR(S) | : Wayne Lederer | |

It is certified that error appears in the above-identified patent and that said Letters Patent is hereby corrected as shown below:

Title page, col 2, under OTHER PUBLICATIONS, delete "Signa I.5T MR," and insert --Signa 1.5T MR,--.

Signed and Sealed this
Fifteenth Day of May, 2012

David J. Kappos
*Director of the United States Patent and Trademark Office*